US009779497B2

(12) United States Patent
Thiagarajan et al.

(10) Patent No.: US 9,779,497 B2
(45) Date of Patent: Oct. 3, 2017

(54) MEASURING GLOMERULAR NUMBER FROM KIDNEY MRI IMAGES

(71) Applicants: Jayaraman Jayaraman Thiagarajan, Dublin, CA (US); Karthikeyan Ramamurthy, Yorktown Heights, NY (US); Andreas Spanias, Tempe, AZ (US); David Frakes, Scottsdale, AZ (US)

(72) Inventors: Jayaraman Jayaraman Thiagarajan, Dublin, CA (US); Karthikeyan Ramamurthy, Yorktown Heights, NY (US); Andreas Spanias, Tempe, AZ (US); David Frakes, Scottsdale, AZ (US)

(73) Assignee: ARIZONA BOARD OF REGENTS, A BODY CORPORATE OF THE STATE OF ARIZONA, ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 14/853,645

(22) Filed: Sep. 14, 2015

(65) Prior Publication Data

US 2016/0005170 A1 Jan. 7, 2016

Related U.S. Application Data

(63) Continuation of application No. PCT/US2014/028279, filed on Mar. 14, 2014.
(Continued)

(51) Int. Cl.
*G06K 9/00* (2006.01)
*G06T 7/00* (2017.01)
(Continued)

(52) U.S. Cl.
CPC ............ *G06T 7/0012* (2013.01); *A61B 5/055* (2013.01); *A61B 5/1075* (2013.01); *A61B 5/20* (2013.01);
(Continued)

(58) Field of Classification Search
CPC ................ G06K 9/00; A61B 5/00; G06T 7/00
(Continued)

(56) References Cited

U.S. PATENT DOCUMENTS 8,023,742 B2 * 9/2011 Brown ................. G06K 9/4609
382/195
9,173,590 B2 * 11/2015 Moats ................... G06T 7/0012
(Continued)

FOREIGN PATENT DOCUMENTS

JP 2012509306 4/2012

OTHER PUBLICATIONS

International Search Report and Written Opinion for co-pending International Application No. PCT/US14/028279 Jul. 24, 2014.
(Continued)

*Primary Examiner* — Abolfazl Tabatabai
(74) *Attorney, Agent, or Firm* — Bryan Cave LLP

(57) ABSTRACT

Measuring the number of glomeruli in the entire, intact kidney using non-destructive techniques is of immense importance in studying several renal and systemic diseases. In particular, a recent Magnetic Resonance Imaging (MRI) technique, based on injection of a contrast agent, cationic ferritin, has been effective in identifying glomerular regions in the kidney. In various embodiments, a low-complexity, high accuracy method for obtaining the glomerular count from such kidney MRI images is described. This method employs a patch-based approach for identifying a low-dimensional embedding that enables the separation of glomeruli regions from the rest. By using only a few images
(Continued)

marked by the expert for learning the model, the method provides an accurate estimate of the glomerular number for any kidney image obtained with the contrast agent. In addition, the implementation of our method shows that this method is near real-time, and can process about 5 images per second.

20 Claims, 11 Drawing Sheets

Related U.S. Application Data

(60) Provisional application No. 61/786,243, filed on Mar. 14, 2013.

(51) Int. Cl.
```
A61B 5/055    (2006.01)
A61B 5/20     (2006.01)
A61B 5/107    (2006.01)
G06K 9/62     (2006.01)
G06T 11/60    (2006.01)
A61P 13/12    (2006.01)
```
(52) U.S. Cl.
CPC ............ *G06K 9/6269* (2013.01); *G06T 11/60* (2013.01); *G06T 2207/10004* (2013.01); *G06T 2207/10088* (2013.01)

(58) Field of Classification Search
USPC ....... 382/128, 129, 130, 131, 132, 133, 134; 514/15.4, 167, 181, 182, 733
See application file for complete search history.

(56) References Cited

U.S. PATENT DOCUMENTS

| | | | |
|---|---|---|---|
| 2003/0083320 A1 | 5/2003 | Doi | |
| 2003/0176330 A1 | 9/2003 | Bandaru et al. | |
| 2006/0127880 A1* | 6/2006 | Harris | G06K 9/00127 435/4 |
| 2008/0137929 A1 | 6/2008 | Chen et al. | |
| 2012/0172344 A1* | 7/2012 | Inada | A61K 31/566 514/181 |
| 2014/0334701 A1* | 11/2014 | Ye | G06T 11/006 382/131 |

OTHER PUBLICATIONS

Athitos, V., Alon, J., Sclaroff, S., and Kollios, G., BoostMap: A Method for Efficient Approximate Similarity Rankings, IEEE Computer Society Conference on Computer Vision and Pattern Recognition 2004.
Beeman, S.C., et al., Measuring Glomerular Number and Size in Perfused Kidneys Using MRI, American Journal of Physiology, Renal Physiology, vol. 300, No. 6, pp. F1454-F1457 Mar. 16, 2011.
Belkin, M., and Niyogi, P., Laplacian Eigenmaps and Spectral Techniques for Embedding and Clustering, Advances in Neural Information Processing Systems 14, pp. 585-591 2001.
Bennett, K.M., et al., MRI of the Basement Membrane Using Charged Nanoparticles as Contrast Agents, Magnetic Resonance in Medicine 60, pp. 564-574 2008.
Bernardis, E., and Yu, S.X., Finding Dots: Segmentation as Popping Out Regions From Boundaries, IEEE Conference on Computer Vision and Pattern Recognition, San Francisco, CA, Jun. 13-18, 2010, pp. 199-206 Jun. 13, 2010.
Bonvalet, J., Champion, M., Wanstok, E, and Berjal, G., Compensatory Renal Hypertrophy in Young Rats: Increase in the Number of Nephrons, Kidney International, vol. 1, pp. 391-396 1972.
Cai, D., He, X., and Han, J., Semi-Supervised Discriminant Analysis, Computer Vision, 2007, ICCV 2007, IEEE 11th International Conference, pp. 1-7 2007.
Chang, Y., Hu, C., Feris, R., and Turk, M., Manifold Based Analysis of Facial Expression, Image and Vision Computing , vol. 24, No. 6, pp. 605-614 Aug. 23, 2005.
Cheng, B., Yang, J., Yan, S., Fu, Y., and Huang, T.S., Learning With L1-Graph for Image Analysis, IEEE Transactions on Image Processing, vol. 19, No. 4, pp. 858-866 Apr. 2010.
Chen, H., Chang, H., and Liu, T., Local Discriminant Embedding and Its Variants, Computer Vision and Pattern Recognition, CVPR 2005, IEEE Computer Society Conference, vol. 2, pp. 846-853 2005.
Danon, D., Goldstein, L., Marikovsky, Y., and Skutelsky, E., Use of Cationized Ferritin as a Label of Negative Charges on Cell Surfaces, J. Ultrastructure Research, vol. 38, pp. 500-510 1972.
Donoho, D.L., and Grimes, C., Hessian Eigenmaps: Locally Linear Embedding Techniques for High-Dimensional Data, Proceedings of the National Academy of Sciences of the United States of America, vol. 100, No. 10, pp. 5591-5596 May 13, 2003.
He, X., Yan, S., Flu, Y., and Zhang, H., Learning a Locality Preserving Subspace for Visual Recognition, Proceedings of the 9th IEEE International Conference on Computer Vision, pp. 385-392 2003.
He, X., and Niyogi, P., Locality Preserving Projections, Advances in Neural Information Processing Systems, vol. 16, pp. 153-160 2004.
Lowe, D., and Tipping, M.E., NeuroScale: Novel Topographic Feature Extraction Using RBF Networks, Advances in Neural Information Processing Systems, pp. 543-549 1997.
Meyer, F., Topographic Distance and Watershed Lines, Signal Processing, vol. 38, pp. 113-125 1994.
Ramirez, I., Sprechmann, P., and Sapiro, G., Classification and Clustering Via Dictionary Learning with Structured Incoherence and Shared Features, IEEE Conference on Computer Vision and Pattern Recognition, pp. 3501-3508 2010.
Roerdink, J.B.T.M, and Meijster, A., The Watershed Transform: Definitions, Algorithms and Parallelization Strategies, Fundamenta Informaticae, vol. 41, pp. 187-228 2001.
Rowels, S., Saul, L.K., and Hinton, G.E., Global Coordination of Local Linear Models, Advances in Neural Information Processing Systems, vol. 2, pp. 889-896 2002.
Saul, L.K., and Roweis, S.T., An Introduction to Locally Linear Embedding, Tech. Rep. 2000.
Seung, H.S., and Lee, D.D., The Manifold Ways of Perception, Science, vol. 290, pp. 2268-2269 Dec. 22, 2000.
Tenenbaum, J.B., deSilva, V., and Langford, J.C., A Global Geometric Framework for Nonlinear Dimensionality Reduction, Science, vol. 290, pp. 2319-2323 Dec. 22, 2000.
Weinberger, K.Q., and Saul, L.K., Unsupervised Learning of Image Manifolds by Semidefinite Programming, International Journal of Computer Vision, vol. 70, No. 1, pp. 77-90 2006.
Yang, M., Face Recognition Using Extended Isomap, IEEE International Conference on Image Processing, pp. 117-120 2002.
Yan, S., et al., Graph Embedding and Extensions: A General Framework for Dimensionality Reduction, IEEE Transactions on Pattern Analysis and Machine Intelligence, vol. 29, No. 1, pp. 40-51 Jan. 2007.
Bertram, J.F., Soosaipillai, M.C., Ricardo, S.D., and Ryan, G.B., Total Numbers of Glomeruli and Individual Glomerular Cell Types in the Normal Rat Kidney, Cell & Tissue Research, pp. 37-45 Jun. 11, 1992.
Hoy, W.E, et al., Nephron Number, Glomerular Volume, Renal Disease and Hypertension, Current Opinions in nephrology and Hypertension, vol. 17, pp. 258-265 2008.
Brenner, B.M., Garcia, D.L., and Anderson, S., Glomeruli and Blood Pressure: Less of One, More the Other?, American Journal of Hypertension, vol. 1, pp. 335-347 1998.

\* cited by examiner

MEASURING GLOMERULAR NUMBER FROM KIDNEY MRI IMAGES

CROSS-REFERENCE TO RELATED APPLICATIONS

This application is a continuation application of International Application No. PCT/US14/28279, which claims priority to filed Mar. 14, 2014, U.S. Provisional Application No. 61/786,243, filed Mar. 14, 2013. The entirety of the above-referenced disclosures is specifically incorporated herein by reference without disclaimer.

TECHNICAL FIELD

This disclosure relates to systems and methods for counting particular features. Certain embodiments relate to systems and methods for counting glomeruli from kidney MRI images, for example.

BACKGROUND

The variations in the number and size of glomeruli have been linked to several renal and systemic diseases. Although approaches such as acid maceration and the dissector/fractionator stereology technique have been used to measure the glomeruli number and size, they require the destruction of the entire kidney. On the other hand, conventional histological methods determine the overall glomeruli statistics by extrapolating the measurements obtained from a few isolated sections. As a result, these methods do not perform direct measurements and cannot localize the identified glomeruli to specific parts of the kidney. Hence, a robust technique was recently developed, based on magnetic resonance imaging (MRI), to non-destructively measure the glomerular number. This method accurately identifies the glomerulus by injecting a contrast agent, cationic ferritin (CF), which causes a decrease in the MRI signal at the location of the glomerulus. It was demonstrated that the glomerular counts obtained from the MRI images were consistent with the standard histological procedures, while making the measurements in the entire kidney.

An efficient computational method that can automatically obtain the glomerular count from the kidney MRI image slices would be beneficial to make this technology viable for clinical use. Although, existing image segmentation methods can be used, due to the characteristics of these images, a more sophisticated procedure would be beneficial.

BRIEF DESCRIPTION OF THE DRAWINGS

To facilitate further description of the embodiments, the following drawings are provided in which.

Figure 1:
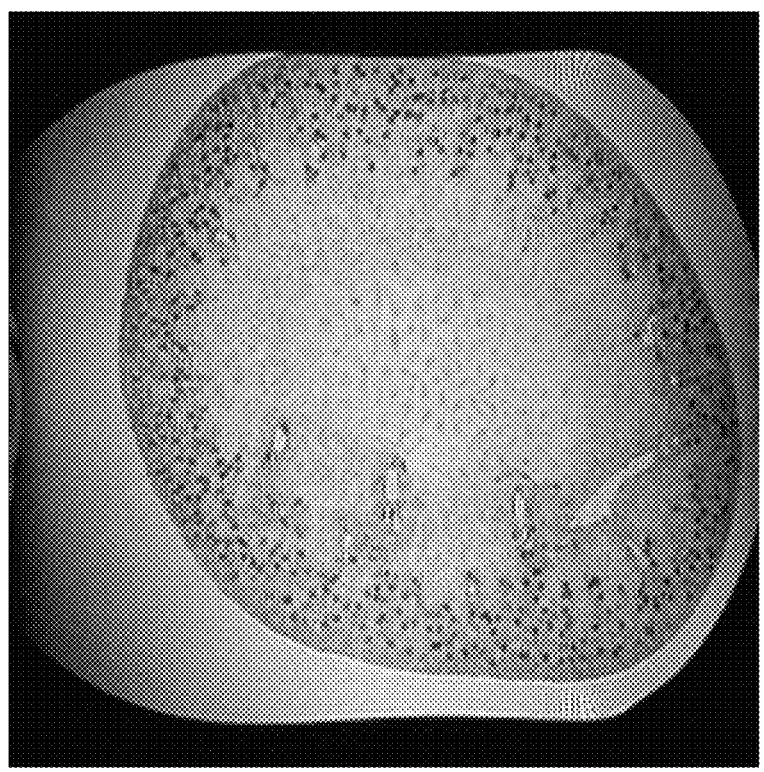
FIG. 1 illustrates a sample axial kidney image from a 3-dimensional magnetic resonance imaging data obtained from a cationic ferritin-injected rat.

For simplicity and clarity of illustration, the drawing figures herein illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types. The absence of the word "removably," "removable," and the like near the word "coupled," and the like does not mean that the coupling, etc. in question is or is not removable.

DESCRIPTION OF EXAMPLES OF EMBODIMENTS

Various embodiments include a method of counting glomeruli in an image of a kidney. The method can be implemented via execution of computer instructions configured to run at one or more processing modules and configured to be stored at one or more non-transitory memory storage modules. The method can include analyzing patches corresponding to each pixel within the image. The method also can include determining, using the patches, whether each pixel belongs to at least one of the glomeruli. The method further can include counting the glomeruli in the image.

A number of embodiments, include a method of counting glomeruli in an image of a kidney. The method can be implemented via execution of computer instructions configured to run at one or more processing modules and configured to be stored at one or more non-transitory memory storage modules. The method can include extracting a first patch centered around each pixel of the image. The method also can include computing a low-dimensional projection for each first patch. The method further can include performing segmentation using K-Means clustering to obtain independent regions. The method also can include counting a total number of the independent regions.

Some embodiments, include a system for counting glomeruli in an image of a kidney. The system can include one or more processing modules and one or more non-transitory memory storage modules storing computing instructions. The computing instruction can be configured to run on the one or more processing modules and perform the certain acts. The computing instructions can perform the act of extracting a first patch centered around each pixel of the image. The computing instructions also can perform the act computing a low-dimensional projection for each first patch. The computing instructions further can perform the act of performing segmentation using K-Means clustering to obtain independent regions. The computing instructions also can perform the act of counting a total number of the independent regions.

This disclosure describes, among other things, examples of certain embodiments, and certain aspects thereof. Other embodiments may differ from the particular examples described in detail herein. In various embodiments, an efficient method is described, for instance, to identify glomerular regions and obtain their count. In addition to being computationally efficient, certain embodiments of this method use expert-marked ground truth to build a highly accurate system. The method described in various embodiments constructs similarity graphs for patches in the MRI images, and learns low-dimensional embeddings to segment the glomerular regions. In order to make these graphs robust to intensity variations across different images, a subspace-based approach can be used. Furthermore, the discrimination power of the method can be improved by considering relations between glomerular and non-glomerular regions in the ground truth images. Results obtained with examples of this method show that it is a computationally simple method that can provide accurate estimates for around 5 images per second.

Measuring the glomerular number in a kidney can be useful to understand a variety of renal and systemic diseases. Several existing approaches to estimate the glomerular number such as acid maceration and the dissector/fractionator stereology technique require the destruction of the entire kidney. Furthermore, histological methods typically extrapolate the total count obtained from a limited number of isolated histological regions. In addition to providing an inaccurate estimate, these methods do not allow for localization of the glomeruli to specific parts of the kidney.

A recent technique that addresses this problem of obtaining the glomerular count non-destructively, from the entire kidney, is based on Magnetic Resonance Imaging (MRI). This method works by injecting a contrast agent, cationic ferritin, prior to acquiring the MRI images of the kidney. Due to the electrostatic binding of the cationic ferritin to the anionic macromolecules of the glomerular basement membrane, there is a decrease in the MRI signal at the glomerular regions. Estimating the number of glomeruli using these MR image slices can be posed as an image segmentation problem. However, many existing segmentation methods are not robust to the intensity variations across the different slices, and are dependent on suitable initialization. Furthermore, incorporating prior knowledge of the ground truth from a few sample images is not straightforward.

In various embodiments, a method to automatically determine the glomerular count from these kidney MRI images is developed. This method adopts a patch-based processing approach, and builds graphs that describe the relations between glomerular and non-glomerular regions in a set of ground-truth images. The robustness of these graphs to intensity variations and measurement noise is improved by building non-local graphs based on sparse representations. By computing a discriminative embedding in the training stage, the need to compute the graph-based embedding for a test image is eliminated. As a result, the computational complexity of performing segmentation, and obtaining the count is significantly reduced. Furthermore, the glomerular count estimated using this method is accurate, and hence can be a valuable tool in translating this MRI imaging technique to clinical practice.

The variations in the number and size of glomeruli have been linked to several renal and systemic diseases. Though approaches such as acid maceration and the dissector/fractionator stereology technique have been used to measure the glomeruli number and size, they require the destruction of the entire kidney. On the other hand, conventional histological methods determine the overall glomeruli statistics by extrapolating the measurements obtained from a few isolated sections. As a result, these methods do not perform direct measurements and cannot localize the identified glomeruli to specific parts of the kidney. Hence, a robust technique based on magnetic resonance imaging (MRI) has been developed to non-destructively measure the glomeruli number and size, as described in S. C. Beeman, M. Zhang, L. Gubhaju, T. Wu, J. F. Bertram, D. H. Frakes, B. R. Cherry, and K. M. Bennett, "Measuring glomerular number and size in perfused kidneys using MRI," *American Journal of Physiology-Renal Physiology*, vol. 300, no. 6, pp. F1454-F1457, 2011 (hereinafter Beeman et al.). In a number of embodiments, this method can accurately identify the glomerulus by injecting cationic ferritin (CF), which causes a decrease in the MRI signal at the location of the glomerulus. Glomerular counts obtained from the 3D MRI images were consistent with the standard histological procedures, while making the measurements in the entire kidney. A sample axial kidney image from a 3-dimensional (3D) magnetic resonance imaging (MRI) data obtained from a cationic ferritin (CF)-injected rat is shown in FIG. 1. The MRI signal is comparatively weak at the locations of the glomerulus.

An automated method for estimating the glomerular count from a kidney MRI image can be developed. A solution to solving this problem is to apply a 3D segmentation method over the slices and identify isolated glomeruli, and subsequently count the number of segmented regions. For simplicity, we will first consider one axial slice (2D image) to obtain the glomerular count, and then extend it to the case of 3D volumetric data. Though the general problem of image segmentation can be unsupervised, we are interested to incorporate some prior knowledge about the MRI image intensities at glomeruli locations in some embodiments. This prior knowledge can be obtained by manually marking glomeruli regions in a few ground truth images. The other important challenge with unsupervised segmentation methods is its computational complexity. By learning a suitable discriminative model from labeled training data, the complexity of segmenting a test image can be reduced significantly, in addition to producing accurate results. Though a variety of segmentation approaches are possible, in different embodiments, we propose a method based on sparse representations. The proposed approach works by extracting small image patches (e.g., size 5×5), and computing a low-dimensional embedding for the patches, such that glomeruli regions are discriminated from the other regions in the MRI image. For a test image, the extracted patches can be projected onto the discriminant directions and passed to a clustering method to identify the glomeruli. Extending this approach to the 3D case is straightforward. Instead of extracting patches from a 2D image, we will obtain patches of size 5×5×5, for example, by considering 5 consecutive axial slices for each 5×5 patch.

Mapping data from high-dimensional input spaces to low-dimensional spaces is beneficial in several computer vision problems. Several dimensionality reduction procedures work by learning appropriate subspaces to efficiently represent the data. However, certain subspace methods are insufficient when Euclidean distance is incapable of describing the intrinsic similarities between the data samples. Furthermore, the inherent geometry of data in several applications can be non-linear. For example, a set of images that vary in rotation or scale reside on a manifold in the original space. When the data samples are densely distributed on a manifold, we can employ manifold learning methods, in a number of embodiments, to infer the underlying inherent structure. A variety of methods that preserve either the global or local properties of the training data can be used for dimensionality reduction and visualization. However, mapping a test sample to the low-dimensional space can be more difficult, when compared to subspace methods. As a result, manifold learning methods are not commonly employed to learn embeddings that can discriminate different classes of data. Some methods address this challenge by finding a mapping for the whole data space, not just for the training samples. However, these methods preserve data localities or similarities in the low-dimensional embedding space, and hence doe not result in class discrimination. As an alternative, some methods consider the geodesic distances between the data samples to perform linear discriminant analysis (LDA).

Another approach for describing the relation between training samples is to construct graphs. Several supervised, semi-supervised, and unsupervised machine learning schemes can be unified under the general framework of graph embedding. In addition, subspace approaches such as principal component analysis, linear discriminant analysis, and locality preserving projections can all be posed as graph embedding problems. Two approaches can be used for graph construction: (i) nearest-neighbor method, where, for each data sample, k nearest neighbors are chosen, and (ii) $\epsilon$-ball based method, where, for each data sample, the samples lying in the $\epsilon$ ball surrounding it are chosen. In both cases, the graph edge weights can be fixed as binary values, Gaussian kernel values or the Euclidean distances directly, as examples. Graph embedding can also be applied to supervised and semi-supervised learning problems, as another example. Local discriminant embedding (LDE) is a supervised embedding scheme that incorporates intra- and inter-class relationships by respectively defining two different graphs, for instance. Furthermore, when only a subset of the training data is labeled, a semi-supervised graph embedding approach, referred to as semi-supervised discriminant analysis (SDA) can be used in some embodiments, as another example.

Though graph construction methods can be successful, in a number of embodiments, their performance can be affected, in particular embodiments, by the following lack of robustness to noise in the data samples. Since the neighbors are identified based on Euclidean distance, noise in even a few data samples can change the graph structure significantly. Performance can be affected by inability to identify distinct neighborhood structure for each data sample, when training data is not equally well samples in different areas of the feature space. Since both the graph construction approaches use a fixed global parameter (k or $\epsilon$) to determine the graph structure, they do not allow the use of data-adaptive neighborhoods.

To address the aforementioned challenges, some embodiments use graphs constructed based on sparse codes of the data samples. Sparse coding aims to obtain a parsimonious representation for the data using the basis functions in a given dictionary. When constructing the $l_1$ graph, we can use the set of training samples as the dictionary directly, instead of inferring from the data. Sparse coding can be robust to noise, and does not include unrelated inhomogeneous data since the choice of neighbors is data dependent. The sparse codes can be obtained using $l_1$ minimization and hence the complexity of constructing the graph is quite high when compared to the classical graph construction approaches. Furthermore, the $l_1$ graph construction approach can be unsupervised, in some embodiments, and does not take into account the label information of the training data in certain embodiments.

Various embodiments obtain discriminative embeddings for patches from the kidney MRI images, using $l_1$ graphs. Though our formulation is for a 2-class case, this can be generalized to multi-class problems as well. The proposed method, in a number of embodiments, allows us to incorporate prior knowledge from the expert-marked ground truth images and eliminates the need to construct the $l_1$ graphs for the test images. As a result, the process of identifying the glomeruli regions, and subsequently obtaining the count, can be computationally efficient, in some embodiments, and provides accurate results, in particular embodiments, in comparison to other segmentation approaches.

Supervised Graph Embedding

The inherent low dimensionality of data can be exploited in order to achieve improved performances in various computer vision and pattern recognition tasks. In recent years, the use of non-linear dimensionality reduction (NLDR) techniques has gained lot of interest. The main aim is to identify a low dimensional manifold onto which high dimensional data can be projected while preserving most of the local and/or global structure. A class of approaches known as manifold clustering and manifold learning methods such as Locally Linear Embedding, Hessian LLE and Laplacian Eigenmaps preserve local information of the manifold. Global methods such as Isomap and semidefinite embedding try to preserve global and local relationships. In addition, approaches such as Locality Preserving Projections (LPP) explicitly learn mapping functions to project data onto low-dimensional spaces. Although the learned embedding can be applicable to test samples, these methods can be more appropriate for clustering problems wherein no supervised information is available. Interestingly, several of these embedding methods can be unified under the framework of graph embedding.

LPP is an unsupervised graph embedding approach that computes projection directions, such that the pairwise distances of the projected training samples in the neighborhood are preserved. Let us define the training data as $\{x_i | x_i \in \Re^M\}_{i=1}^T$. An undirected graph G is defined, with the training samples as vertices, and the similarity between the neighboring training samples coded in the affinity matrix $W \in \Re^{T \times T}$. Let us denote the graph Laplacian as $L = D - W$, where D is a degree matrix with each diagonal element containing the sum of the corresponding row or column of L. The d projection directions for LPP, $V \in \Re^{M \times d}$, can be computed by optimizing $$\min_{trace(V^T X D X^T V) = I} trace(V^T X L X^T V). \quad (1)$$

Here X is a matrix obtained by stacking all data samples as its columns. The embedding for any data sample x can be obtained by projecting onto the orthonormal directions V as $V^T x$. It can be shown that LPP computes the projection directions by minimizing the objective $$\min_V \sum_{i,j=1}^T \|V^T x_i - V^T x_j\|_2^2 w_{ij} \quad \text{s.t.} \quad \sum_{i=1}^T \|V^T x_i\|_2^2 \delta_{ij} = 1. \quad (2)$$

This optimization ensures that the embedding preserves the neighborhood structure of the graph.

However, there is a need to incorporate class label information to learn an embedding that can discriminate different classes of data. Linear Discriminant Analysis (LDA) is such a supervised graph embedding framework that uses the within-class and between-class scatter matrices to obtain discriminative projections. Let us assume that the class labels corresponding to the set of training samples, $\{x_i | x_i \in \Re^M\}_{i=1}^T$, are known and denoted by $\{y_i | y_i \in \{1, 2, \ldots, C\}\}_{i=1}^T$. Here C indicates the total number of classes.

In order to pose LDA as a graph embedding problem, we compute the intra-class and inter-class graphs as follows:

$$w_{ij} = \begin{cases} \frac{1}{T_{y_i}} & \text{if } y_i = y_j, \\ 0 & \text{otherwise.} \end{cases} \quad (3)$$

Here $T_{y_i}$ denotes the total number of samples with the label $y_i$.

$$w'_{ij} = \frac{1}{T}. \quad (4)$$

Using these affinity matrices, we construct the diagonal degree matrices D and D', whose elements are computed as $d_{ii} = \Sigma_j w_{ij}$ and $d'_{ii} = \Sigma_j w'_{ij}$ respectively. Finally, the graph Laplacian matrices are obtained as $L = D - W$ and $L' = D' - W'$. Given the two graph laplacian matrices, the low-dimensional embedding is computed as $$\max_V \frac{Tr[V^T L' V]}{Tr[V^T L V]}. \quad (5)$$

Note that, the reduced number of dimensions d is fixed at C−1. The above optimization computes an embedding such that the between class scatter is maximized, while minimizing the within-class scatter. LDA aims to solve a trace-ratio maximization problem and this can be converted to an equivalent ratio-trace maximization problem, $Tr[(V^T LV)^{-1} V^T L'V]$. A greedy solution for this problem can be obtained using the generalized eigenvalue decomposition $$XL'X^T = \lambda XLX^T. \quad (6)$$

The set of directions V is computed as the d top eigenvectors.

Alternatively, the affinity matrices can be constructed by considering both the class label information and the local structure of the data samples. Let $N_k(i)$ denote the set of k-nearest neighbors for the data sample $x_i$. The affinity matrices are then constructed as $$w_{ij} = \begin{cases} 1 & \text{if } y_i = y_j \text{ AND } [i \in N_k(j) \text{ OR } j \in N_k(i)], \\ 0 & \text{otherwise.} \end{cases} \quad (7)$$

$$w'_{ij} = \begin{cases} 1 & \text{if } y_i \neq y_j \text{ AND } [i \in N'_k(j) \text{ OR } j \in N'_k(i)], \\ 0 & \text{otherwise.} \end{cases} \quad (8)$$

Given the affinity matrices, the embedding can be obtained as in the case of LDA. This approach is referred to as local discriminant embedding (LDE)

Proposed Method

In this section, an example of a proposed method for measuring the glomerular number is described. By using sparse codes to define the relation between data samples, more robust graphs can be constructed for unsupervised and supervised learning tasks. In particular, certain embodiments perform discriminative embedding using $l_1$ graphs. We begin by discussing the construction of $l_1$ graphs and subsequently the training and testing stages of the proposed method.

Constructing $l_1$ Graphs

In sparse modeling, data is represented as a sparse linear combination of atoms from a "dictionary" matrix. The dictionary is typically overcomplete, i.e., the number of basis functions exceeds the data dimension and hence we need to solve an underdetermined system of linear equations. The linear generative model for sparse modeling of a data sample $x \in \Re^M$ is given by, $$x = \Psi a \quad (9)$$

where $\Psi \in \Re^{M \times K}$ is the set of K elementary features and $\alpha \in \Re^K$ (is the coefficient vector. Though different forms of regularization can be applied to this problem, a sparse solution is more robust and can be effective for recovering the data sample x. If we assume that the coefficient vector is sparse and has statistically independent components, the elements of the dictionary $\Psi$ can be inferred from the generative model using appropriate constraints. Considering the generative model for sparse coding (9), the codes can be obtained either by minimizing the exact $l_0$ penalty or its convex surrogate $l_1$ penalty as, $$(PL0) \hat{a} = \underset{a}{\operatorname{argmin}} \|a\|_0 \text{ subj. to } x = \Psi a, \quad (10)$$

$$(PL1) \hat{a} = \underset{a}{\operatorname{argmin}} \|a\|_1 \text{ subj. to } x = \Psi a, \quad (11)$$

where $\|\cdot\|_0$ is the $l_1$ norm and $\|\cdot\|_1$ is the $l_1$ norm. Since real-world data cannot be expressed exactly using the generative model in (9), usually the equality constraints in (10) and (11) are replaced using the constraint $\|x - \Psi a\|_2^2 \leq \epsilon$, where $\epsilon$ is the error goal of the representation. The exact $l_0$ minimization given in (10) is a combinatorial problem and that is the major reason why its convex surrogate is often used.

Given a set of unlabeled training samples $X = \{x_i\}_{i=1}^T$, the $l_1$ graph can be constructed as follows. For each data sample $x_i$, we solve the $l_1$ optimization problem to obtain the sparse codes, $$\underset{a_i}{\min} \|a_i\|_1, \text{ s.t. } x_i = \Psi^i a_i. \quad (12)$$

Figure 2:
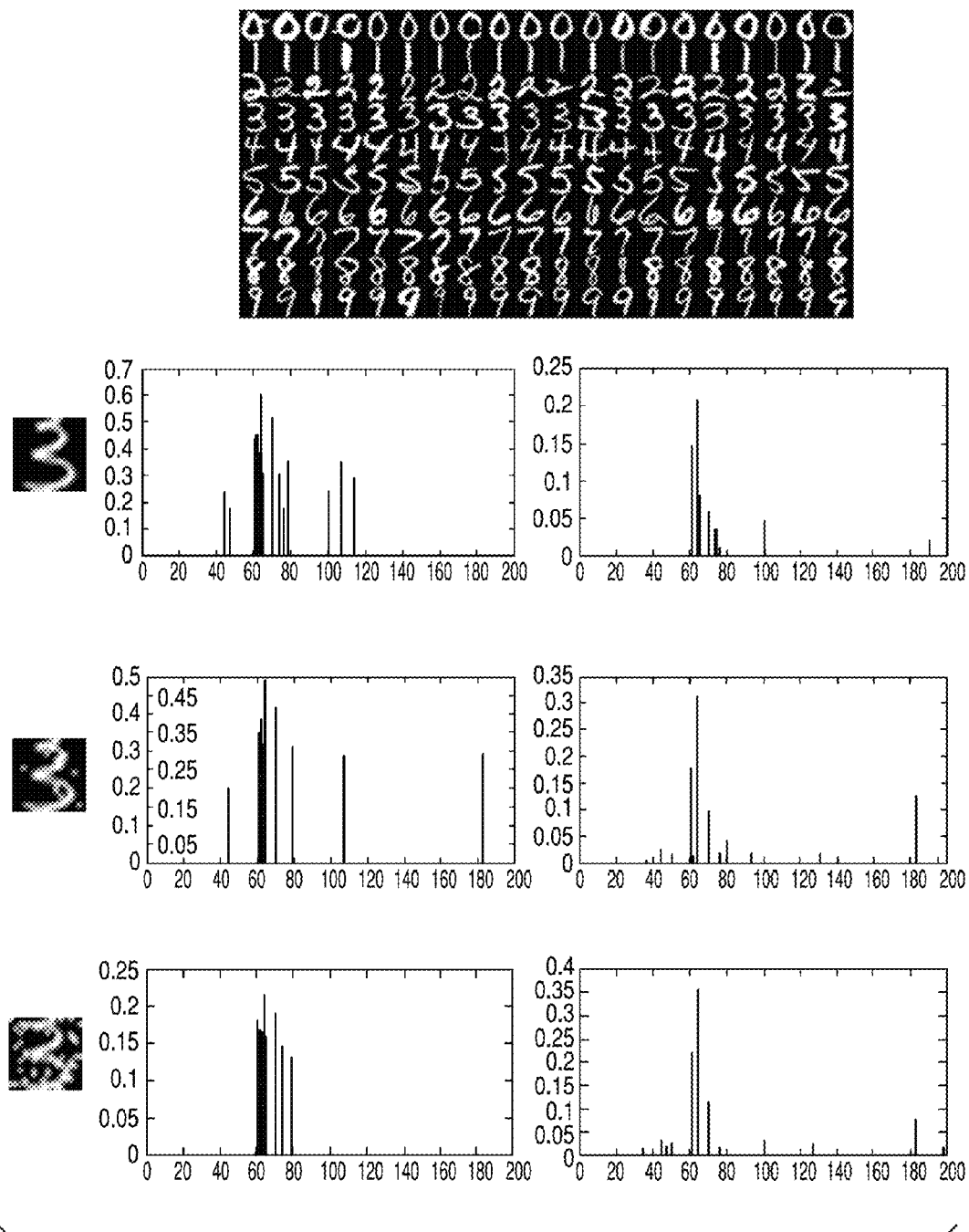
FIG. 2 illustrates the similarities between one of the training samples and the rest, obtained using nearest neighbors and sparse representation.

Here the dictionary $\Psi^i = [x_1, \ldots, x_i, x_{i+1}, \ldots, x_T]$ is designed as the set of training samples, leaving out the sample $x_i$. The importance of a training sample in representing another sample is used as the indicator for similarity between these two samples. Hence, representation coefficients can be used to build the similarity matrix for the graph. Since the entries of this weight matrix represent the similarities between data samples, we can assume them to be non-negative. Hence, the $l_1$ minimization can be solved with non-negative constraints on the coefficient values. Let us denote this process of computing the sparse coefficient matrix as $A = SC(X, X)$, where the first argument is the data matrix, and the second argument is the dictionary matrix. Using the sparse coefficient matrix, $A \in \Re^{T \times T}$, as the similarity matrix, we construct the Laplacian for the graph as $L = (\Pi - A)^T (\Pi - A)$. Here, $\Pi$ denotes the identity matrix of size $T \times T$. This Laplacian matrix can be subsequently used to perform spectral clustering. In order to demonstrate the robustness of sparse representations, we consider a subset of images from the USPS handwritten digit dataset ("USPS dataset"), available at ftp://ftp.kyb.tuebingen.mpg.de/pub/bs/data/. FIG. 2 demonstrates the robustness of an $l_1$ graph, and shows the similarities between one of the training samples and the rest, obtained using nearest neighbors and sparse representation. The set of training samples used for this simulation are obtained from the USPS dataset. For an example data sample (Digit 3), its similarities to all data samples in the case of a K-Nearest neighbor (K-NN) graph (left) and a $l_1$ graph (right) are shown. As the data sample is corrupted by noise, the K-NN graph changes significantly while the $l_1$ graph is robust to the noise. Using sparse coding can provide a more robust graph even when the data sample is noisy.

Incorporating Supervisory Information

The $l_1$ graph construction is unsupervised, and hence supervisory information cannot be incorporated. The problem of identifying glomeruli in the kidney images can be solved using spectral clustering with $l_1$ graphs. However, such an approach poses two main challenges: (i) prior knowledge about the intensities in the glomeruli regions cannot be used, and (ii) computational complexity of building an $l_1$ graph is high. In some embodiments, embedding using a set of training images is used and a low-complexity method is used for estimating the glomerular number in any test image.

In order incorporate supervisory information, we can first build a training set, in a number of embodiments, by manually marking the glomerular regions in a few kidney MRI images. The training stage of the method can work with image patches of size 5×5, for example, extracted from the training images. Patches can be extracted around every pixel in the image, in some embodiments, and those patches centered at the pixels marked as belonging to glomeruli regions are considered to be positive examples ($X_{pos}$). The rest of the patches are marked as negative examples ($X_{neg}$). Our goal, in a number of embodiments, is to create a low-dimensional embedding that discriminates the positive and negative examples effectively. Local discriminant embedding addresses this problem by building graphs as described above. In order to obtain a more robust embedding, we propose to use $l_1$ graphs.

As a preprocessing step, all training patches are normalized to unit $l_2$ norm. Optionally, mean removal can also be performed prior to normalization. Following this, we compute four different similarity (sparse coefficient) matrices for constructing the $l_1$ graph using the procedure described above: (i) $A_{p,p} = SC(X_{pos}, X_{pos})$, (ii) $A_{p,n} = SC(X_{pos}, X_{neg})$, (iii) $A_{n,p} = SC(X_{neg}, X_{pos})$, and (iv) $A_{n,n} = SC(X_{neg}, X_{neg})$. In order to use these similarities to discriminate between the two classes, we propose to construct intra-class and inter-class similarity matrices as follows.

$$A = \begin{bmatrix} A_{p,p} & 0_{T_p, T_n} \\ 0_{T_n, T_p} & A_{n,n} \end{bmatrix} \quad (13)$$

$$A' = \begin{bmatrix} 0_{T_p, T_p} & A_{p,n} \\ A_{n,p} & 0_{T_n, T_n} \end{bmatrix} \quad (14)$$

The corresponding laplacian matrices are computed as $$L = (\Pi - A)^T (\Pi - A), \quad (15)$$

$$L' = (\Pi - A')^T (\Pi - A'). \quad (16)$$

Figure 3:
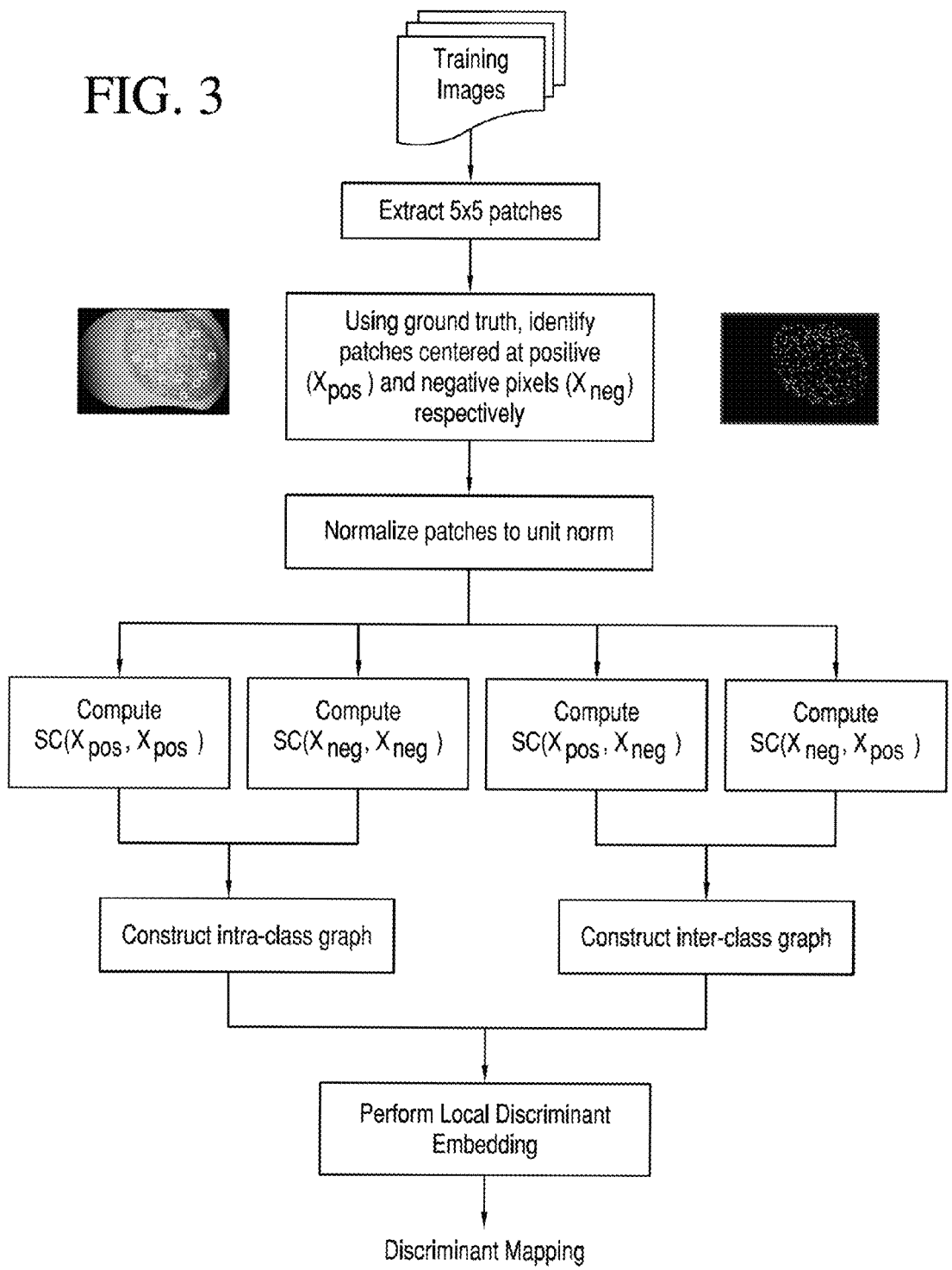
FIG. 3 illustrates a proposed algorithm for computing an embedding that discriminates image patches containing glomeruli from the rest, using a process of computing a discriminant embedding using $l_1$ graphs, according to an embodiment.
Figure 4:
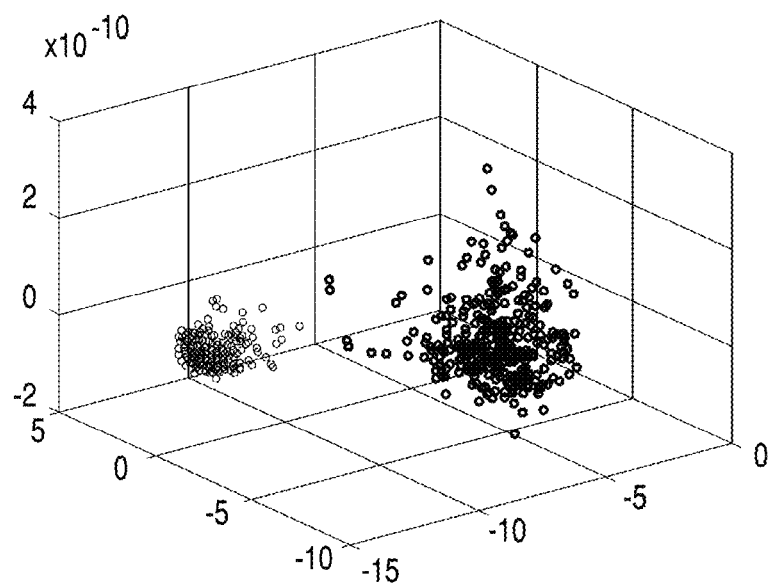
FIG. 4 illustrates an example demonstration for the proposed supervised graph embedding approach, and shows the 3-dimensional embedding of the training images and it can be seen that the two classes are well separated (top), and the features obtained using the identified mapping for test images (bottom)
Figure 4:
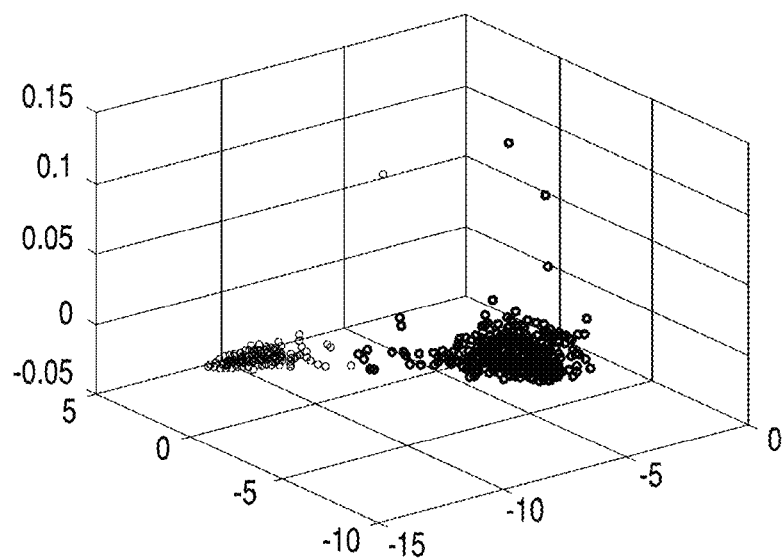

By creating a low-dimensional projection V, we are interested in preserving the intra-class relationships, while making samples from different classes to be dissimilar. This is achieved by performing local discriminant embedding with L and L' respectively as shown in (5). FIG. 3 describes the proposed algorithm for computing an embedding that discriminates image patches containing glomeruli from the rest, using a process of computing a discriminant embedding using $l_1$ graphs. The method works by constructing $l_1$ graphs to model inter-class and intra-class relationships, and performing local discriminant embedding. In order to demonstrate the behavior of the proposed embedding approach, we build an example dataset using images from 2 different classes (Digits 3 and 7) in the USPS dataset. In each class, we use 300 randomly chosen images for training and the rest for testing. FIG. 4 illustrates an example demonstration for the proposed supervised graph embedding approach. This simulation uses 2 classes of digits from the USPS dataset, and divides them into train/test sets. Using the training images, we compute the discriminant mapping and obtain the low-dimensional features for both the training and test images. FIG. 4 (top) shows the 3-dimensional embedding of the training images and it can be seen that the two classes are well separated. By using the identified mapping for test images, we obtain the features in FIG. 4 (bottom). The compactness of the classes observed in the test images reflects the discrimination power of the proposed embedding. Moreover, the compactness of samples within a class, and separation between the two classes reflects the discrimination power of the proposed embedding.

Obtaining Glomerular Count

Figure 5:
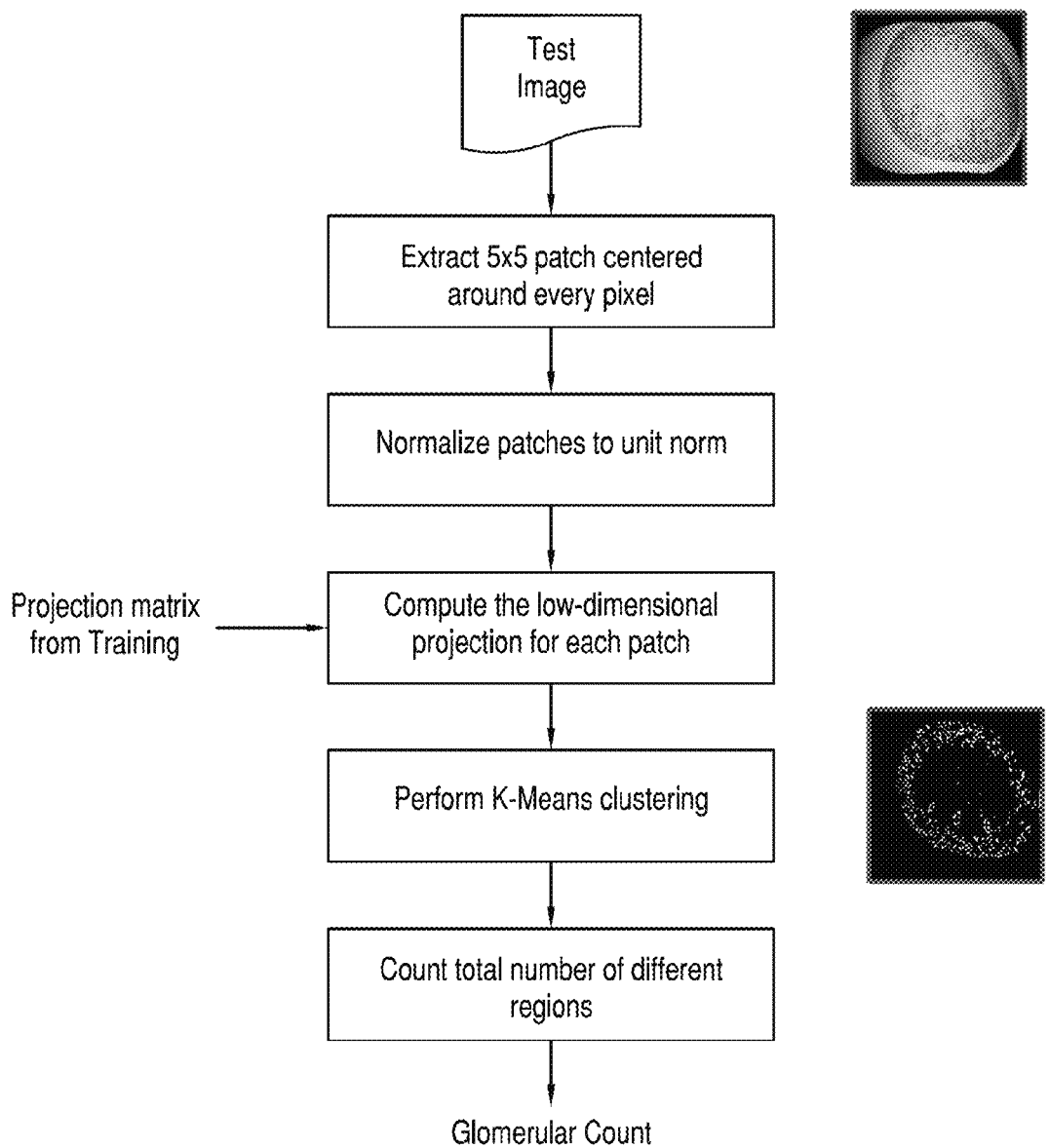
FIG. 5 illustrates a procedure for obtaining the glomerular count in a test image, according to another embodiment.

Since we have learned a discriminant embedding, computing low-dimensional features for a test image can be straightforward. Unlike conventional sparse coding methods, in a number of embodiments, we need not compute sparse codes for the test image patches. As a result, the proposed method, in certain embodiments, works in near real-time, and processes an image of 256×256 in just around 0.2 seconds (s). Given a test image, in particular embodiments, we extract 5×5 patches similar to the training stage, and normalize them to unit $l_1$ norm. Following this we project the vectorized patches onto the discriminant directions as $V^T Z$, where Z denotes the matrix of patches from a test image. Using these low-dimensional features, we employ the simple K-means clustering procedure to perform segmentation. Given the segmented image, we count the number of independent regions with at least more than r pixels. This implies that we assume that the glomeruli regions contain at least r pixels in its neighborhood, so that we can ignore a few lonely false positives provided by certain embodiments of the method. The steps involved in obtaining the glomerular count for a test image is illustrated in FIG. 5. Specifically, FIG. 5 shows a low-complexity procedure for obtaining the glomerular count in a test image. The discriminant mapping determined in the training stage is used with the test image patches directly, and hence there is no need to obtain the sparse codes.

Experiments

Dataset

For evaluating the performance of the proposed method, we use the dataset reported in Beeman et al. Furthermore, the estimated glomerular number is compared against the results obtained using the MRI segmentation used in Beeman et al., acid maceration, and stereological methods. We now briefly describe the procedure for obtaining the dataset. Additional details on the materials and methods can be found in Beeman et al. Cationic Ferritin was synthesized and male Sprague-Dawley rats, weighing between 215 and 245 grams (g), were given three intravenous bolus doses. Kidneys were perfused and fixed via transcardial perfusion of phosphate buffered saline (PBS) followed by 10% neutral buffered formalin, then resected and stored in glutaraldehyde. The perfused left kidneys were imaged in glutaraldehyde on a Varian 19T 89-mm-bore nuclear magnetic resonance (NMR) (Varian, Palo Alto, Calif.), equipped with a DOTY 3-axis imaging probe and a gradient with a maximum strength of 300 G/cm (DOTY Scientific, Columbia, S.C.). Scans were acquired with a 3D gradient echo (GRE) sequence with echo time/repetition time=7/40 milliseconds (ms) and a resolution of 62×62×78 micrometers (μm). Total scan time was 6 hours/kidney.

Benchmark Method

Labeled glomeruli in the 3D MRI data set can be counted using the method used in Beeman et al. Using bicubic interpolation, images in the data set were resized and the spatial resolution was changed to 31×31×62 μm. Spatial signal magnitude gradients were computed to identify significant spatial changes in signal magnitude throughout the volume. Only voxels exceeding a threshold on the signal magnitude difference were included for the subsequent operations. Following this, regional minima were located in these areas using an upper signal magnitude threshold. Regions in the image considered to be glomeruli were then labeled based on morphological thresholds. Note that, here it is assumed that a glomerulus is approximately spherical. Finally, the watershed transform was computed on these regions to distinguish individual glomeruli where signal overlap of multiple glomeruli might occur.

Results

In this section, we report the results obtained using the proposed method in this example, in comparison to the benchmark technique with MRI images, acid maceration, and stereology methods. The evaluation was carried out with three different subjects (Rat A, Rat B and Rat C) and the glomerular count for the MRI based approaches were obtained from 192 slices. Note that the results reported for the proposed method were obtained using only 2-D slices. For training the discriminant mapping, 5 ground truth images were used and patches of size 5×5 were extracted. Using the ground truth labels, a training set containing 7,500 positive and 7,500 negative example patches was generated. The patches were normalized, and the four $l_1$ graphs were constructed with the sparsity penalty λ fixed at 0.2. The number of reduced dimensions d was fixed at 10 and the mapping $V \in \Re^{25 \times 10}$ was obtained using the method described in FIG. 3. For each image in the evaluation dataset, the normalized 5×5 patches were projected onto the discriminant directions, and K-means clustering was performed to identify the glomeruli. Finally, the number of independent regions was counted and reported as the glomerular number.

Figure 6:
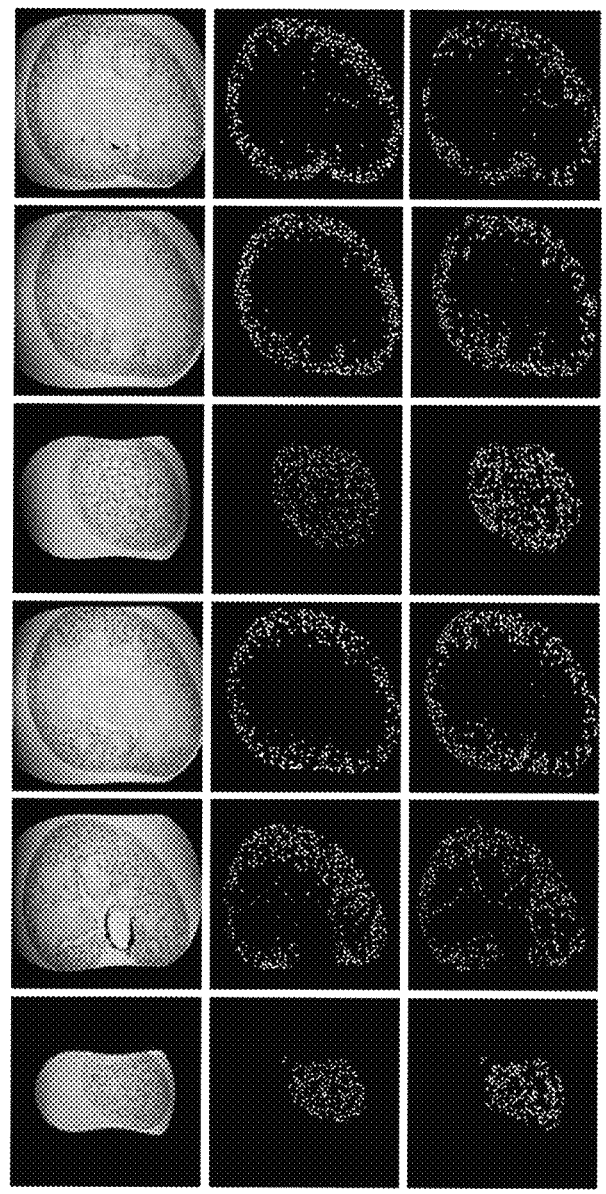
FIG. 6 illustrates the segmentation obtained for a set of test images, showing from left to right, (a) the original kidney image with reduced intensities at glomeruli locations; (b) the ground truth image with manually labeled glomeruli regions; and (c) segmentation obtained using the approach proposed according to an embodiment.

FIG. 6 illustrates the segmentation obtained for a set of test images, using the proposed method. From left to right on each row, FIG. 6 shows: (a) the original kidney image with reduced intensities at glomeruli locations; (b) the ground truth image with manually labeled glomeruli regions; and (c) segmentation obtained using the approach proposed in this disclosure. In each case, both the original and ground truth images are shown for comparison. Clearly, the proposed method provides impressive results in determining the glomeruli regions and the glomeruli count is comparable to the manual count. The glomerular counts for the three evaluation datasets are shown in Table 1. Specifically, Table 1 shows glomerular court obtained using acid maceration, stereology, and the MRI techniques, for three different datasets. Each dataset consisted of 192 images and total glomerular count is shown. In addition, the total time taken, in seconds, to process each dataset using the proposed algorithm is shown. The results obtained using the proposed method, in this example, are comparable to the stereology results, and the variance is comparatively lower. Another important advantage of the proposed scheme is its low computational complexity, which is evident from the time reported in Tablet 1. The time complexity was measured in MATLAB R2012a on a 2.8 GHz, Intel i7 desktop.

TABLE 1

| Dataset | MRI Number (Beeman et al.) | Maceration Number | Stereology Number | Proposed Algorithm | Total Time Taken (seconds) |
| --- | --- | --- | --- | --- | --- |
| Rat A | 32,789 | 27,504 | 34,504 | 33,884 | 41.1 |
| Rat B | 35,203 | 31,190 | 35,421 | 34,335 | 42.4 |
| Rat C | 31,772 | 31,075 | | 32,117 | 44.9 |
| Rat D | 39,482 | 33,321 | | 34,765 | 40.3 |
| Rat E | 29,682 | 31,478 | | 35,208 | 46.6 |
| Mean | 33,786 | 30,914 | 34,963 | 34,062 | 43.1 |
| Standard Deviation (STD) | 3,753 | 2,112 | 648 | 1,193 | 2.6 |

Aspects of Particular Embodiments

Certain aspects of particular embodiments include:
1. Employs a graph-based embedding approach to exploit the similarities between small patches extracted from the kidney MRI images.
2. Expert-marked ground truth images are used to learn a discriminative embedding. This is achieved by considering relations between glomerular and non-glomerular regions.
3. The graphs are made robust to intensity-variations across several images by adopting a non-local, subspace approach. The weights in the graph are obtained based on sparse representations of the patches. In addition to intensity variations, the method is robust to measurement noise in the images.
4. The procedure pre-computes projection directions using training patches, and for each patch in an actual test image the low-dimensional embeddings is obtained using an inner product operation.
5. The final glomeruli identification is performed using simple centroid-based clustering procedures, such as k-means, on the low-dimensional embeddings of patches.

Advantages Over Prior Technology and Impact

In contrast to prior segmentation methods that use local models to identify glomerular regions, certain embodiments of the present disclosure use a non-local graph based approach that is robust to intensity variations across the various slices in the kidney MRI image.

Many existing segmentation methods use clustering schemes which are sensitive to initialization. However, the proposed method incorporates ground truth information provided by the expert user to create embeddings that discriminate well between glomerular and non-glomerular patches. Hence it is much less sensitive to initialization.

Since the ground truth information provided by the expert is used to identify discriminative projection directions, for a test image, there is no need to compute graph relations between patches in a test image. Simple clustering techniques are used, in a number of embodiments, to obtain the number of glomeruli.

For a test image, certain embodiments of the proposed method use a computationally simple method to create low-dimensional embeddings and perform clustering to identify the glomerular count. The results from our implementation show that particular embodiments can process about 5 images per second. The proposed method, in various embodiments, can be implemented using sophisticated parallel implementations to achieve ultra-high speed glomerular counting, for example.

Figure 7:
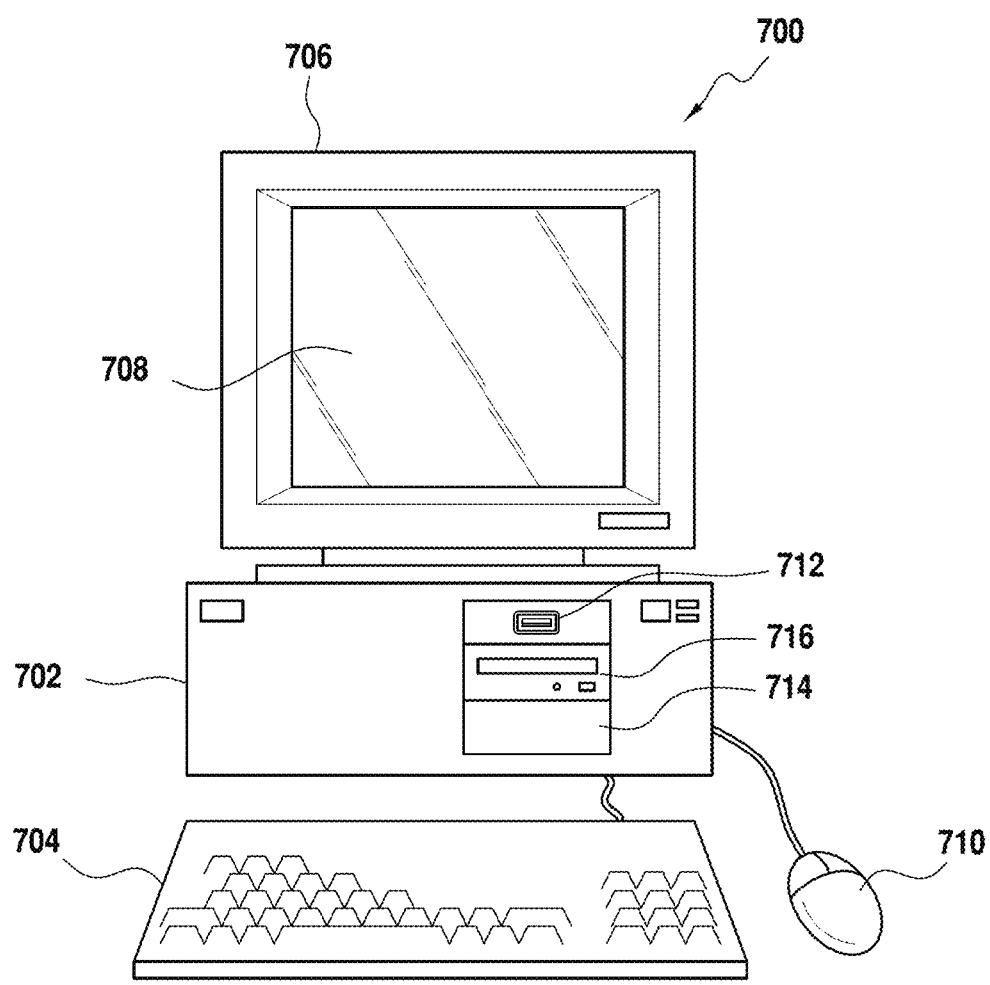
FIG. 7 illustrates a computer system that is suitable for implementing an embodiment of the computer system illustrated in FIG. 12, and for implementing one or more embodiments of the methods disclosed herein.
Figure 8:
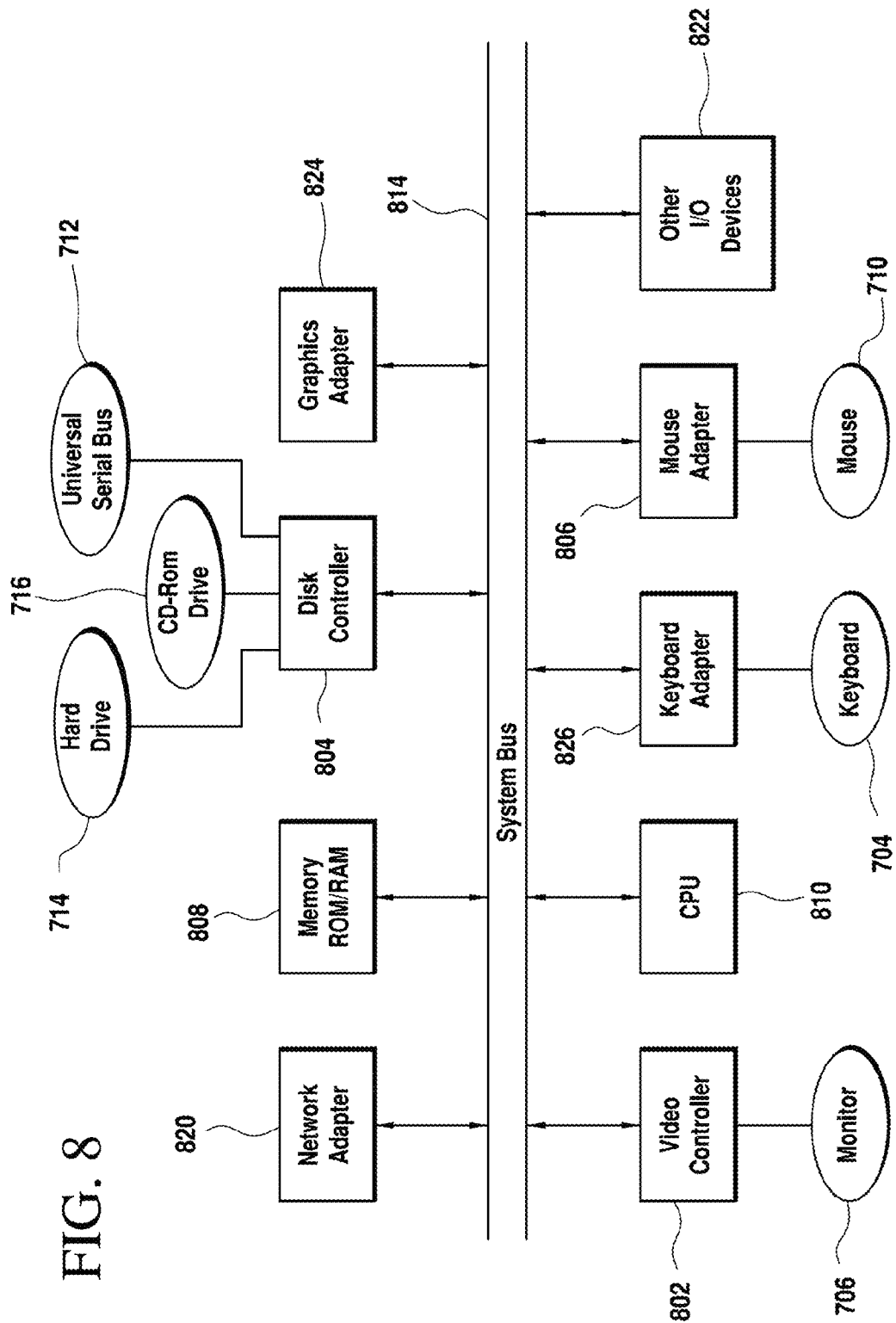
FIG. 8 illustrates a representative block diagram of an example of the elements included in the circuit boards inside a chassis of the computer system of FIG. 7.

FIG. 7 illustrates an exemplary embodiment of computer system 700, all of which or a portion of which can be suitable for implementing the techniques described above. As an example, a different or separate one of chassis 702 (and its internal components) can be suitable for implementing the techniques described above. Furthermore, one or more elements of computer system 700 (e.g., refreshing monitor 706, keyboard 704, and/or mouse 710, etc.) can also be appropriate for implementing the techniques described above. Computer system 700 comprises chassis 702 containing one or more circuit boards (not shown), Universal Serial Bus (USB) port 712, Compact Disc Read-Only Memory (CD-ROM) and/or Digital Video Disc (DVD) drive 716, and hard drive 714. A representative block diagram of the elements included on the circuit boards inside chassis 702 is shown in FIG. 8. Central processing unit (CPU) 810 in FIG. 8 is coupled to system bus 814 in FIG. 8. In various embodiments, the architecture of CPU 810 (FIG. 8) can be compliant with any of a variety of commercially distributed architecture families.

Continuing with FIG. 8, system bus 814 also is coupled to memory storage unit 808, where memory storage unit 808 comprises both read only memory (ROM) and random access memory (RAM). Non-volatile portions of memory storage unit 808 or the ROM can be encoded with a boot code sequence suitable for restoring computer system 700 (FIG. 7) to a functional state after a system reset. In addition, memory storage unit 808 can comprise microcode such as a Basic Input-Output System (BIOS). In some examples, the one or more memory storage units of the various embodiments disclosed herein can comprise memory storage unit 808, a USB-equipped electronic device, such as, an external memory storage unit (not shown) coupled to universal serial bus (USB) port 712 (FIGS. 7-8), hard drive 714 (FIGS. 7-8), and/or CD-ROM or DVD drive 716 (FIGS. 7-8). In the same or different examples, the one or more memory storage units of the various embodiments disclosed herein can comprise an operating system, which can be a software program that manages the hardware and software resources of a computer and/or a computer network. The operating system can perform basic tasks such as, for example, controlling and allocating memory, prioritizing the processing of instructions, controlling input and output devices, facilitating networking, and managing files. Some examples of common operating systems can comprise Microsoft® Windows® operating system (OS), Mac® OS, UNIX® OS, and Linux® OS.

As used herein, "processor" and/or "processing module" means any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions. In some examples, the one or more processors of the various embodiments disclosed herein can comprise CPU 810.

In the depicted embodiment of FIG. 8, various I/O devices such as disk controller 804, graphics adapter 824, video controller 802, keyboard adapter 826, mouse adapter 806, network adapter 820, and other I/O devices 822 can be coupled to system bus 814. Keyboard adapter 826 and mouse adapter 806 are coupled to keyboard 704 (FIGS. 7-8) and mouse 710 (FIGS. 7-8), respectively, of computer system 700 (FIG. 7). While graphics adapter 824 and video controller 802 are indicated as distinct units in FIG. 8, video controller 802 can be integrated into graphics adapter 824, or vice versa in other embodiments. Video controller 802 is suitable for refreshing monitor 706 (FIGS. 7-8) to display images on a screen 708 (FIG. 7) of computer system 700 (FIG. 7). Disk controller 804 can control hard drive 714 (FIGS. 7-8), USB port 712 (FIGS. 7-8), and CD-ROM drive 716 (FIGS. 7-8). In other embodiments, distinct units can be used to control each of these devices separately.

In some embodiments, network adapter 820 can comprise and/or be implemented as a WNIC (wireless network interface controller) card (not shown) plugged or coupled to an expansion port (not shown) in computer system 700 (FIG. 7). In other embodiments, the WNIC card can be a wireless network card built into computer system 700 (FIG. 7). A wireless network adapter can be built into computer system 700 (FIG. 7) by having wireless communication capabilities integrated into the motherboard chipset (not shown), or implemented via one or more dedicated wireless communication chips (not shown), connected through a PCI (peripheral component interconnector) or a PCI express bus of computer system 700 (FIG. 7) or USB port 712 (FIG. 7). In other embodiments, network adapter 820 can comprise and/or be implemented as a wired network interface controller card (not shown).

Although many other components of computer system 700 (FIG. 7) are not shown, such components and their interconnection are well known to those of ordinary skill in the art. Accordingly, further details concerning the construction and composition of computer system 700 (FIG. 7) and the circuit boards inside chassis 702 (FIG. 7) are not discussed herein.

When computer system 700 in FIG. 7 is running, program instructions stored on a USB-equipped electronic device connected to USB port 712, on a CD-ROM or DVD in CD-ROM and/or DVD drive 716, on hard drive 714, or in memory storage unit 808 (FIG. 8) are executed by CPU 810 (FIG. 8). A portion of the program instructions, stored on these devices, can be suitable for carrying out at least part of the techniques described above.

Although computer system 700 is illustrated as a desktop computer in FIG. 7, there can be examples where computer system 700 may take a different form factor while still having functional elements similar to those described for computer system 700. In some embodiments, computer system 700 may comprise a single computer, a single server, or a cluster or collection of computers or servers, or a cloud of computers or servers. Typically, a cluster or collection of servers can be used when the demand on computer system 700 exceeds the reasonable capability of a single server or computer.

Figure 9:
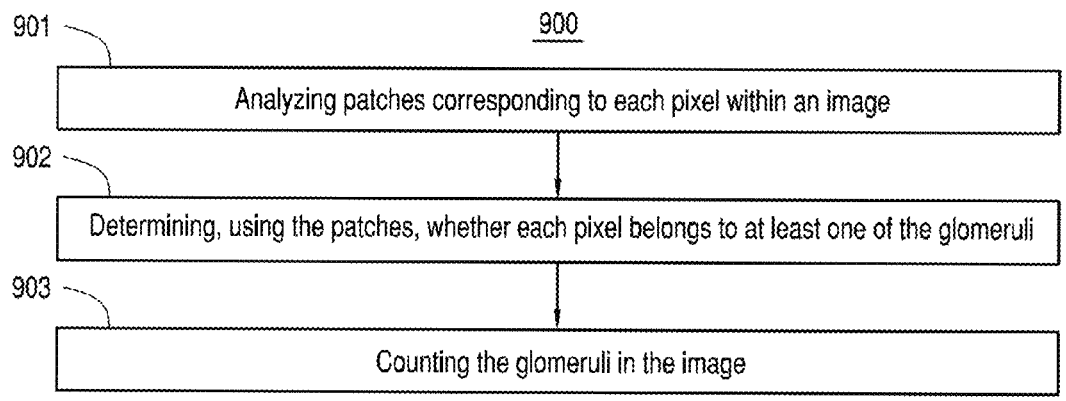
FIG. 9 illustrates a flow chart for a method of counting glomeruli in an image of a kidney, according to another embodiment.

Turning ahead in the drawings, FIG. 9 illustrates a flow chart for a method 900 of counting glomeruli in an image of a kidney, according to an embodiment. Method 900 is merely exemplary and is not limited to the embodiments presented herein. Method 900 can be employed in many different embodiments or examples not specifically depicted or described herein. In some embodiments, the procedures, the processes, and/or the activities of method 900 can be performed in the order presented. In other embodiments, the procedures, the processes, and/or the activities of method 900 can be performed in any suitable order. In still other embodiments, one or more of the procedures, the processes, and/or the activities of method 900 can be combined or skipped. In some embodiments, method 900 can be implemented via execution of computer instructions configured to run at one or more processing modules and configured to be stored at one or more non-transitory memory storage modules. For example, method 900 can be implemented by computer system 700 (FIG. 7).

Referring to FIG. 9, in some embodiments method 900 can include block 901 of analyzing patches corresponding to each pixel within the image. In certain embodiments, the image can be a test image. In other embodiments, the image can be a training image. In some embodiments, the patches can be centered on each pixel. In a number of embodiments, the patches can be small image patches from a 2D image, such as 5×5 patches or 7×9 patches. In other embodiments, the patches can be of other sizes and/or dimensions. For example, in another embodiment, the patches can be of size 5×5×5 in a 3D image. In many embodiments, each of extracted patches can be projected onto discriminant directions, as described above. In some embodiments, projection directions can be computed using training patches. In various embodiments, for each patch in the image, low dimensional embeddings can be obtained using an inner product operations, as described above. In a number of embodiments, method 900 can be robust to measurement noise in the image.

In various embodiments, a graph-based embedding approach, as described above, can be used to exploit similarities between the patches. In certain embodiments, the graphs are made robust to intensity variations across several images. As described above, weights in the graphs can be obtained based on sparse representations of the patches. In several embodiments, method 900 can include using expert-marked ground truth to learn a discriminative embedding, as described above. In some embodiments, method 900 can include considering relations between glomerular and non-glomerular regions. In a number of embodiments, method 900 can include adopting a non-local subspace approach, as described above.

Method 900 also can include block 902 of determining, using the patches, whether each pixel belongs to at least one of the glomeruli. As described above, glomeruli identification can be performed using K-Means clustering. In other embodiments, glomeruli identification can be performed using another suitable process.

Method 900 also can include block 903 of counting the glomeruli in the image. As described above, counting the glomeruli can be accomplished, in many embodiments, by counting the number of different regions in the K-Means clustering. In certain embodiments, method 900 can include displaying at least a portion of the glomeruli on a screen, such as screen 708 (FIG. 7). For example, the glomeruli can be displayed on screen 708 as shown in the various examples of FIG. 6. As a specific example, the glomeruli can be displayed on screen 708 as shown in the third column (from left to right) in FIG. 6.

Figure 10:
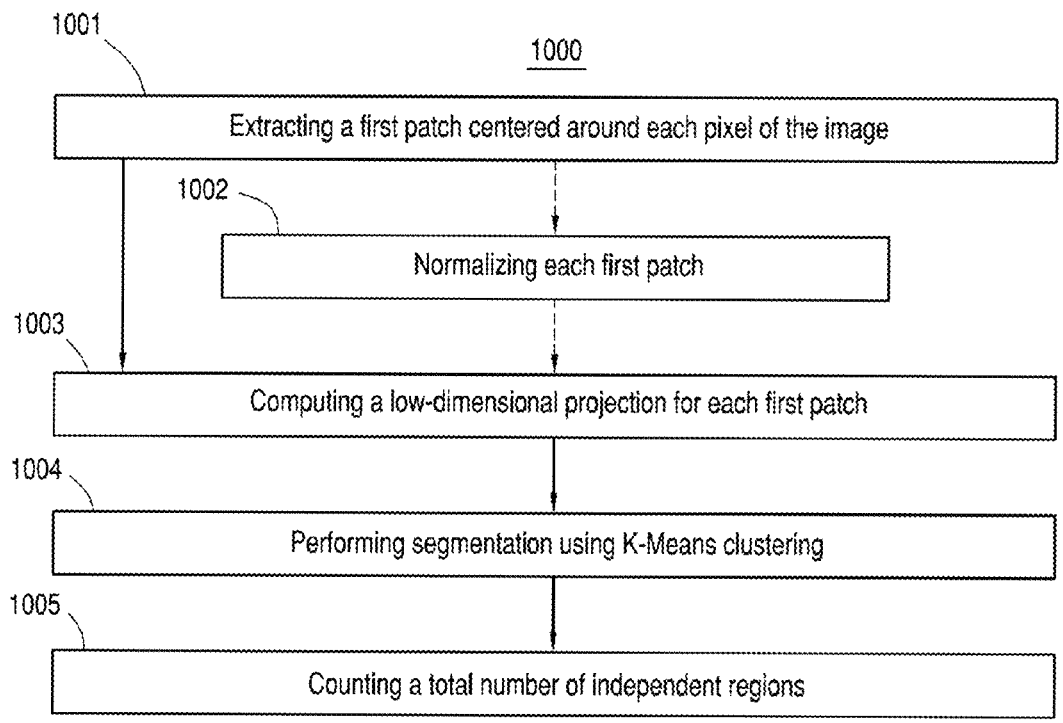
FIG. 10 illustrates a flow chart for a method of counting glomeruli in an image of a kidney, according to another embodiment.

Turning ahead in the drawings, FIG. 10 illustrates a flow chart for a method 1000 of counting glomeruli in an image of a kidney, according to an embodiment. Method 1000 is merely exemplary and is not limited to the embodiments presented herein. Method 1000 can be employed in many different embodiments or examples not specifically depicted or described herein. In some embodiments, the procedures, the processes, and/or the activities of method 1000 can be performed in the order presented. In other embodiments, the procedures, the processes, and/or the activities of method 1000 can be performed in any suitable order. In still other embodiments, one or more of the procedures, the processes, and/or the activities of method 1000 can be combined or skipped. In some embodiments, method 1000 can be implemented via execution of computer instructions configured to run at one or more processing modules and configured to be stored at one or more non-transitory memory storage modules. For example, method 1000 can be implemented by computer system 700 (FIG. 7).

Referring to FIG. 10, in some embodiments method 1000 can include block 1001 of extracting a first patch centered around each pixel of the image. In a number of embodiments, the image can be a test image. In some embodiments, the first patches can be centered on each pixel. In several of embodiments, the first patches can be 5 pixels by 5 pixels or 6 pixels by 9 pixels. In other embodiments, the patches can be of other sizes and/or dimensions. For example, in another embodiment, the patches can be of size 5 pixels by 5 pixels by 5 pixels in a 3D image.

Method 1000 also can include block 1002 of normalizing each first patch. For example, as described above, each first patch can be normalized to unit $l_1$ norm. In some embodiments, block 1002 can occur after block 1001. In other embodiments, block 1002 can be skipped.

Method 1000 also can include block 1003 of computing a low-dimensional projection for each first patch. For example, as described above, block 1003 can include projecting the vectorized patches onto discriminant directions. In a number of embodiments, computing the low-dimensional projection for each first patch can be based at least in part on a projection matrix obtained from training images, as described above. In some embodiments, block 1003 can be performed directly after performing block 1001 without performing block 1002. In other embodiments, block 1003 can be performed after performing block 1002.

Method 1000 also can include block 1004 of performing segmentation using K-Means clustering to obtain independent regions, as described above. In many embodiments, the segmentation can use the low-dimensional projections obtained in block 1003.

Method 1000 also can include block 1005 of counting a total number of the independent regions. For example, the independent regions segmented in block 1004 can be counted for independent regions with at least a certain number of pixels, which can advantageously prevent counting of lonely false positives.

Figure 11:
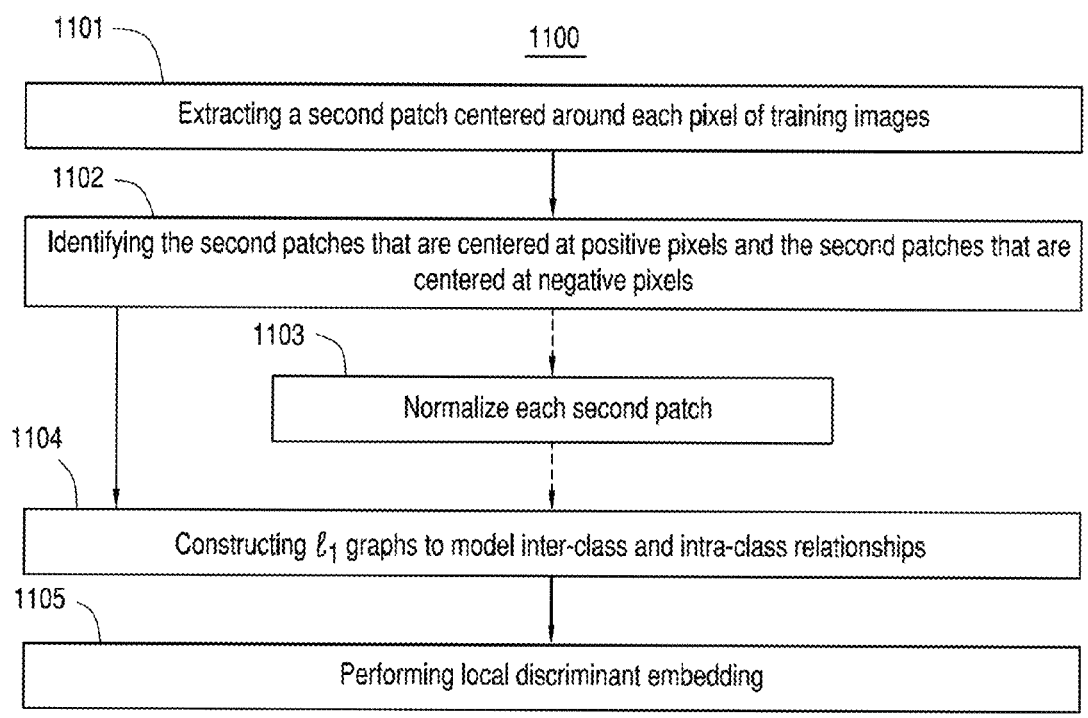
FIG. 11 illustrates a flow chart for a method of counting glomeruli in an image of a kidney, according to another embodiment.

Turning ahead in the drawings, FIG. 11 illustrates a flow chart for a method 1100 of counting glomeruli in an image of a kidney, according to an embodiment. Method 1100 is merely exemplary and is not limited to the embodiments presented herein. Method 1100 can be employed in many different embodiments or examples not specifically depicted or described herein. In some embodiments, the procedures, the processes, and/or the activities of method 1100 can be performed in the order presented. In other embodiments, the procedures, the processes, and/or the activities of method 1100 can be performed in any suitable order. In still other embodiments, one or more of the procedures, the processes, and/or the activities of method 1100 can be combined or skipped. In some embodiments, method 1100 can be implemented via execution of computer instructions configured to run at one or more processing modules and configured to be stored at one or more non-transitory memory storage modules. For example, method 1100 can be implemented by computer system 700 (FIG. 7). In a number of embodiments, method 1100 can be performed prior to performing method 1000 (FIG. 10), and/or can be used by method 1000 (FIG. 10).

Referring to FIG. 11, in some embodiments method 1100 can include block 1101 of extracting a second patch centered around each pixel of training images. For example, as described above, patches can be extracted around every pixel in the image. In some embodiments, the first patches can be centered on each pixel. In several of embodiments, the first patches can be 5 pixels by 5 pixels or 7 pixels by 3 pixels. In other embodiments, the patches can be of other sizes and/or dimensions. For example, in another embodiment, the patches can be of size 5 pixels by 5 pixels by 5 pixels in a 3D image.

Method 1100 also can include block 1102 of identifying the second patches that are centered at positive pixels and the second patches that are centered at negative pixels using expert-marked ground truth images. For example, as described above, those patches centered at the pixels marked as belonging to glomeruli regions can be identified as positive examples ($X_{pos}$). The other patches can be identified as negative examples ($X_{neg}$).

Method 1100 also can include block 1103 of normalizing each second patch. For example, as described above, normalizing can be performed as a preprocessing step to creating a low-dimensional embedding. In various embodiments, each second patch can be normalized to unit $l_2$ norm. In some embodiments, mean removal can be performed prior to normalization, as described above. In some embodiments, block 1103 can occur after block 1102. In other embodiments, block 1103 can be skipped.

Method 1100 also can include block 1104 of constructing $l_1$ graphs to model inter-class and intra-class relationships. As described above, intra-class and inter-class similarity matrices can be constructed as using equations (13) and (14) and the corresponding Laplacian matrices can be computed using equations (15) and (16). In a number of embodiments, as described above, using $l_1$ graphs can beneficially facilitate a more robust embedding. In some embodiments, block 1104 can be performed directly after performing block 1102 without performing block 1103. In other embodiments, block 1104 can be performed after performing block 1103.

Method 1100 also can include block 1105 of performing discriminant embedding. In many embodiments, local discriminant embedding can be performed as shown in (5). In many embodiments, the discriminant embedding obtained in block 1105 can be used in block 1003 (FIG. 10) of computing a low-dimensional projection for each first patch of the image.

Figure 12:
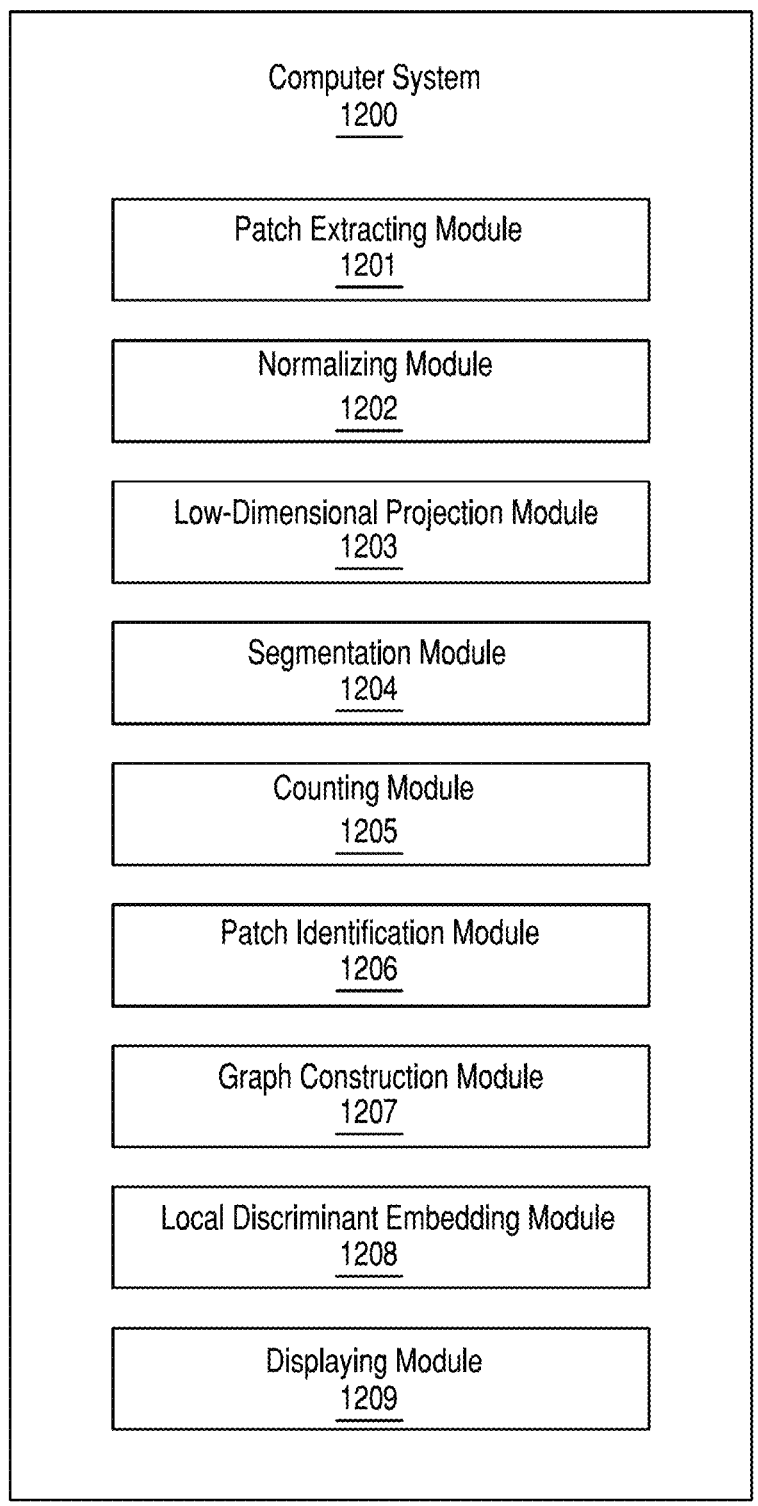
FIG. 12 illustrates a block diagram of computer system, according to another embodiment.

Turning ahead in the drawings, FIG. 12 illustrates a block diagram of computer system 1200, according to an embodiment. Computer system 1200 can be employed in many different embodiments or examples not specifically depicted or described herein. In some embodiments, certain elements or modules of computer system 1200 can perform various procedures, processes, and/or acts. In other embodiments, the procedures, processes, and/or acts can be performed by other suitable elements or modules. In some embodiments, computer system 1200 can be identical or similar to computer system 700 (FIG. 7).

In a number of embodiments, computer system 1200 can include a patch extracting module 1201. In certain embodiments, patch extracting module 1201 can partially or fully perform one or more of block 1001 (FIG. 10) of extracting a first patch centered around each pixel of the image and/or block 1101 (FIG. 11) of extracting a second patch centered around each pixel of training images. In some embodiments, computer system 1200 can include a normalizing module 1202. In certain embodiments, normalizing module 1202 can partially or fully perform one or more of block 1002

(FIG. 10) of normalizing each first patch and/or block 1103 (FIG. 11) of normalizing each second patch.

In various embodiments, computer system 1200 can include a low-dimensional projection module 1203. In certain embodiments, low-dimensional projection module 1203 can partially or fully perform block 1003 (FIG. 10) of computing a low-dimensional projection for each first patch. In many embodiments, computer system 1200 can include a segmentation module 1204. In certain embodiments, segmentation module 1204 can partially or fully perform one or more of block 1004 (FIG. 10) of performing segmentation using K-Means clustering.

In a number of embodiments, computer system 1200 can include a counting module 1205. In certain embodiments, counting module 1205 can partially or fully perform one or more of block 903 (FIG. 9) of counting the glomeruli in the image and/or block 1005 (FIG. 10) of counting the total number of independent regions. In some embodiments, computer system 1200 can include a patch identification module 1206. In certain embodiments, patch identification module 1206 can partially or fully perform block 1102 (FIG. 11) of identifying the second patches that are centered at positive pixels and the second patches that are centered at negative pixels.

In various embodiments, computer system 1200 can include a graph construction module 1207. In certain embodiments, graph construction module 1207 can partially or fully perform block 1104 (FIG. 11) of constructing $l_1$ graphs to model inter-class and intra-class relationships. In several embodiments, computer system 1200 can include a local discriminant embedding module 1208. In certain embodiments, local discriminant embedding module can partially or fully perform block 1105 (FIG. 11) of performing local discriminant embedding. In many embodiments, computer system 1200 can include a displaying module 1209. In certain embodiments, displaying module 1209 display at least a portion of the glomeruli on a screen, such as screen 708 (FIG. 7).

Various embodiments of the subject matter described herein include various combinations of the acts, structure, components, and features described herein, shown in the drawings, or that are known in the art. Moreover, certain procedures can include acts such as manufacturing, obtaining, or providing components that perform functions described herein or in the documents that are incorporated by reference. Furthermore, various embodiments include advertising and selling products that perform functions described herein, that contain structure described herein, or that include instructions to perform functions described herein, as examples. Such products may be obtained or provided through distributors, dealers, or over the Internet, for instance. The subject matter described herein also includes various means for accomplishing the various functions or acts described herein, in the documents that are incorporated by reference, or that are apparent from the structure and acts described.

Further, as used herein, the word "or", except where indicated otherwise, does not imply that the alternatives listed are mutually exclusive. Even further, where alternatives are listed herein, it should be understood that in some embodiments, fewer alternatives may be available, or in particular embodiments, just one alternative may be available, as examples.

Although measuring glomeruli number from kidney MRI images has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that any element of FIGS. 1-12 may be modified, and that the foregoing discussion of certain of these embodiments does not necessarily represent a complete description of all possible embodiments.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A method of counting glomeruli in an image of a kidney, the method being implemented via execution of computer instructions configured to run at one or more processors and configured to be stored at one or more non-transitory computer-readable media, the method comprising:
   extracting a second patch centered around each pixel of training images;
   identifying the second patches that are centered at positive pixels and the second patches that are centered at negative pixels using expert-marked ground truth images;
   constructing $l_1$ graphs to model inter-class and intra-class relationships;
   performing local discriminant embedding;
   analyzing patches corresponding to each pixel within the image;
   determining, using the patches, whether each pixel within the image belongs to at least one of the glomeruli; and
   counting the glomeruli in the image.

2. The method of claim 1, further comprising:
   using graph-based embedding to exploit similarities between the patches.

3. The method of claim 1, further comprising:
   considering relations between glomerular and non-glomerular regions.

4. The method of claim 1, further comprising:
   adopting a non-local subspace approach.

5. The method of claim 1, wherein:
   the method is robust to measurement noise in the image.

6. The method of claim 1, wherein:
   projection directions are pre-computed using training patches.

7. The method of claim 1, further comprising:
   for each patch in the image, obtaining low dimensional embeddings using an inner product operation.

8. The method of claim 1, further comprising:
performing glomeruli identification using K-Means clustering.

9. The method of claim 1, further comprising:
displaying at least a portion of the glomeruli on a screen.

10. The method of claim 1, wherein:
the $l_1$ graphs are made robust to intensity variations across several images.

11. The method of claim 10, wherein:
weights in the $l_1$ graphs are obtained based on sparse representations of the patches.

12. A method of counting glomeruli in an image of a kidney, the method being implemented via execution of computer instructions configured to run at one or more processors and configured to be stored at one or more non-transitory computer-readable media, the method comprising:
extracting a second patch centered around each pixel of training images;
identifying the second patches that are centered at positive pixels and the second patches that are centered at negative pixels using expert-marked ground truth images;
constructing $l_1$ graphs to model inter-class and intra-class relationships;
performing local discriminant embedding;
extracting a first patch centered around each pixel of the image;
computing a low-dimensional projection for the each first patch;
performing segmentation using K-Means clustering to obtain independent regions; and
counting a total number of the independent regions.

13. The method of claim 12, wherein:
the first patches are each 5 pixels by 5 pixels.

14. The method of claim 12, further comprising:
normalizing the each first patch.

15. The method of claim 12, wherein:
computing the low-dimensional projection for the each first patch is based at least in part on a projection matrix obtained from the training images.

16. The method of claim 12, further comprising:
normalizing each second patch centered around each pixel of the training images.

17. A system for counting glomeruli in an image of a kidney, the system comprising:
one or more processors; and
one or more non-transitory computer-readable media storing computing instructions configured to run on the one or more processors and perform:
extracting a second patch centered around each pixel of training images;
identifying the second patches that are centered at positive pixels and the second patches that are centered at negative pixels using expert-marked ground truth images;
constructing $l_1$ graphs to model inter-class and intra-class relationships;
performing local discriminant embedding;
extracting a first patch centered around each pixel of the image;
computing a low-dimensional projection for the each first patch;
performing segmentation using K-Means clustering to obtain independent regions; and
counting a total number of the independent regions.

18. The system of claim 17, wherein:
the first patches are each 5 pixels by 5 pixels.

19. The system of claim 17, wherein the computing instructions are further configured to perform:
normalizing the each first patch.

20. The system of claim 17, wherein:
computing the low-dimensional projection for the each first patch is based at least in part on a projection matrix obtained from the training images; and
the computing instructions are further configured to perform:
normalizing each second patch centered around each pixel of the training images.

* * * * *